Figures 1, 2:
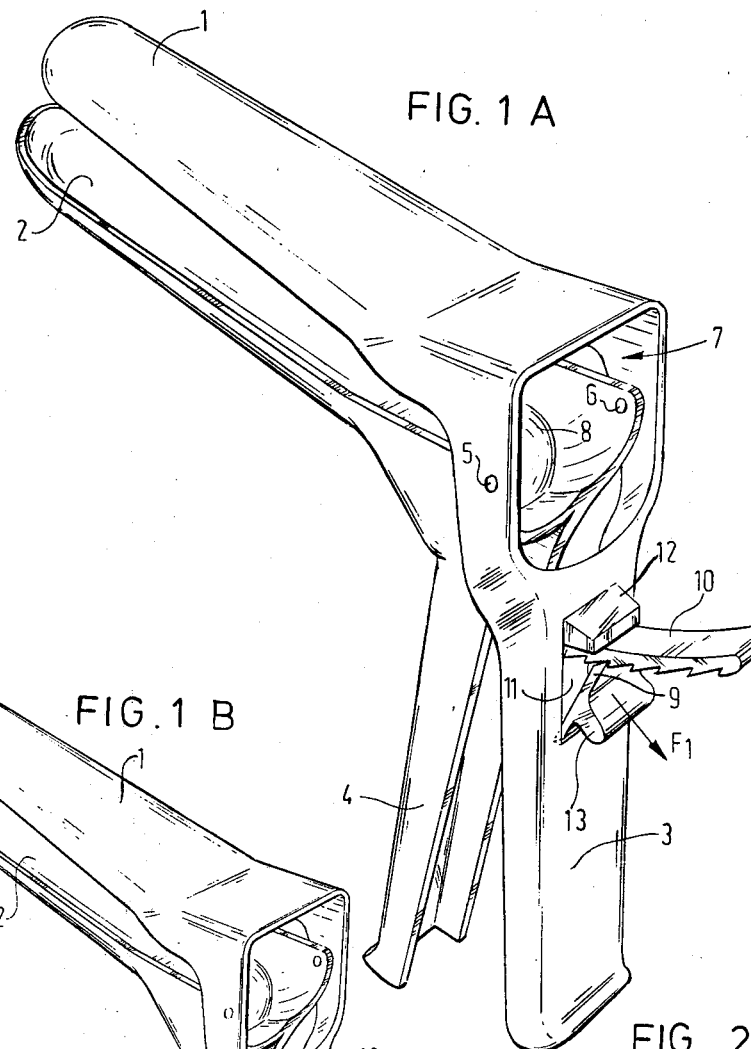

United States Patent [19]

Danz

[11] 4,385,626
[45] May 31, 1983

[54] SPECULUM FOR MEDICAL EXAMINATION WITH A NOISELESS MECHANICAL LOCKING MECHANISM

[75] Inventor: Peter Danz, CJ Haren, Netherlands

[73] Assignee: Lamaf-Kunststoffen B.V., Groningen, Netherlands

[21] Appl. No.: 81,299

[22] Filed: Oct. 2, 1979

[30] Foreign Application Priority Data

Oct. 12, 1978 [NL] Netherlands .......................... 7810273

[51] Int. Cl.³ ................................................ A61B 1/32
[52] U.S. Cl. ..................................................... 128/17
[58] Field of Search ........................................ 128/3–5, 128/17–19, 341, 345, 242, 244, 321, 346; 81/130 A, 130 R, 131, 135, 136, 315, 318, 319, 324, 325, 329

[56] References Cited

U.S. PATENT DOCUMENTS 2,620,697 12/1952 Sarvie ................................... 81/319
4,206,750 6/1980 Kaivola ................................. 128/17

FOREIGN PATENT DOCUMENTS 1080448 8/1967 United Kingdom .
1337830 11/1973 United Kingdom .
1408382 10/1975 United Kingdom .
1477227 6/1977 United Kingdom .
2001854 2/1979 United Kingdom .

Primary Examiner—Richard J. Apley
Assistant Examiner—J. L. Kruter
Attorney, Agent, or Firm—Allison C. Collard; Thomas M. Galgano

[57] ABSTRACT

A speculum for the examination of body cavities, said speculum comprising duck-bill-shaped spreading members and co-operating locking elements to hold the speculum in an adjusted open condition, said locking elements being so biased as to stay clear from one another when in rest, but being adapted to engage with one another only by a conscious action of the user of the speculum.

5 Claims, 3 Drawing Figures

SPECULUM FOR MEDICAL EXAMINATION WITH A NOISELESS MECHANICAL LOCKING MECHANISM

The invention relates to a speculum comprising two relatively movable, e.g. slidably or pivotally cooperating spreading members which are adapted, when used, to be inserted into a body cavity and to be adjusted thereupon in an open position, two operating members associated with the respective spreading members and means for the temporary locking of the spreading members in optionally determinable spread positions, said means being provided with a first locking element associated and adapted to be moved together with one of the spreading members and with a second locking element associated and adapted to be moved together with the other spreading member, said two locking elements being constructed for mutual engagement in a number of discrete locking positions which each define the extent of opening of the speculum and said locking elements being under relative initial stress before the spreading members are brought into spread positions.

Such specula are at present, especially when intended for the large-scale examination of the uterus cervix of women of the likely age categories, mostly at least for the greater part made of synthetic material, so that the speculum need neither be used more than once nor be sterilized thereafter.

In the specula used up to now, e.g. those of the type described in the U.S. Pat. No. 3,815,585, the two mentioned locking elements are often constructed respectively as a catch provided on one operating member and as a toothed member provided on the other operating member, said catch being a kind of ratchet pawl which is adapted to be engaged in various discrete locking positions. After such a speculum has been inserted into the vagina, the two spreading members are put, by means of the operating members which are handled by one hand or both hands, into the desired spread positions, in which the two locking elements become mutually engaged by means of a mechanism or by stress exerted by the tissue. In practice it appears that owing to the mentioned initial stress the two locking elements often move, during their movement before arriving at their desired spread positions, with a rasping or rattling noise one over the other. In many cases this noise appears not to assist the peace of mind of the patient and to interfere with the examination.

Generally this disadvantage does not appear in the speculum disclosed in the U.S. Pat. No. 3,752,149. It is true that therein, during the spreading of the spreading members, forces which could cause the undesired noise are exerted on these members and through them on the locking elements by the tissue. However, appropriate handling of the operating members makes it possible to neutralize these forces and to effect the spreading without the undesired noise. For instance, in a speculum as described in the last mentioned specification it is possible to use a member which is to be operated by the thumb not only for spreading the spreading members but also for the previous and simultaneous disengagement of the locking elements. However, for that purpose some special effort and skill of the examiner are required. Should the examiner not be able to do so, say by fatigue occuring after a nunber of examinations, the undesired noise will be still produced.

The invention has the object to avoid almost entirely the possibility of producing this undesired phenomenon and to provide a speculum which can be handled easily, that means without making heavy demands on the examiner, and without undesired side-effects being produced.

To this end it is proposed in accordance with the invention to use a speculum of the type described in the preamble the mentioned initial stress to force the locking elements away from each other and to have this stress overcome, on the attainment of desired spread positions of the spreading members, by a conscious action for the mutual engagement of the locking elements only. It will be apparent that in the speculum according to the invention no undesired noises of working are produced. Another advantage of the use of an initial stress for forcing the locking elements away from one another is that after the completion of the examination a short suppression or neutralization of the closing forces exerted on the spreading members by the body tissue brings about the automatical disengagement of the two locking elements.

Although not necessary in all cases, it is recommended according to the invention to provide or to form, in several embodiments, on a locking element a member for consciously carrying out the relative movement of said locking element in the direction of engagement.

The measures according to the invention and described hereinbefore may be used in specula having various kinds of locking elements. This is particularly true for a speculum of the type, in which one locking element is a toothed member and the other locking element is a projection, a tooth or a catch adapted to engage with said toothed member for locking purposes. In accordance with the invention such a speculum must be provided, on the locking element or the catch, with a surface to be contacted by the thumb for forcing the element or the catch in the direction of engagement with the catch or the locking element, respectively.

As already was observed hereinbefore the invention relates substantially to specula which are made for the greater part of synthetic material and are meant to be used only once. However, according to the invention the measures described hereinbefore may principally also be applied to metal specula. It will be obvious that, when two locking elements respectively associated with the spreading members and adapted to lock same in a number of discrete positions are used, the invention has the object to so construct the locking members as to ensure that, during the spreading of a speculum, they cannot produce undesired noises.

The invention will be elucidated in the following description of some embodiments illustrated in the accompanying drawing. However, the invention is not restricted to these embodiments. In the drawing:

FIG. 1A shows a perspective view of an embodiment of the invented speculum, of which the locking elements are in mutual engagement, FIG. 1B shows, on a smaller scale, also a perspective view of the speculum illustrated in FIG. 1 having its locking elements disengaged, and FIG. 2 illustrates diagrammatically and on a larger scale a sectional view of a detail of another embodiment of a speculum according to the invention.

The speculum shown in FIGS. 1A and 1B comprises two spreading members 1 and 2 which are made of synthetic material, rounded off on their outer side and hollow on their inner side. These spreading members together form the shape of a duck bill and are meant to be inserted into a body cavity to be examined and thereupon to be brought into an appropriate spread condition. To that end the two spreading members 1 and 2 are respectively integral with their handles 3 and 4 which in the described embodiment extend at angles of 90° and are pivotally interconnected at their upper ends by means of hinge parts 5 and 6 made of synthetic material or metal. Through the window 7 left in the upper end portion of the handle 3 inspection of the cavity 8 of the duck bill and, when the latter is open, also of the body cavity to be examined is possible.

In order to be able to lock the spreading members 1 and 2 in a condition suitable for the examination, after they have been inserted into a body cavity, said members 1 and 2 are provided with locking elements. In the described embodiment these elements are respectively formed as a catch 9 which is flexibly connected with the handle 3 and is bevelled at its free end and as a toothed rack 10 which is provided on the handle 4 and extends towards the handle 3 and through a window 11 thereof. The catch 9 and the rack 10 are so constructed as to be able to engage each other in a number of discrete positions which each correspond with an individual open condition of the speculum (see FIG. 1A) and are meant to fix the adjusted condition. In the spread position of the spreading members 1 and 2, in which the tissue (not shown in the drawing) surrounding the expanded body cavity tries to force the members 1 and 2 towards and the handles 3 and 4 away from each other, the bevelled free end of the catch 9 is pushed into the toothed rack 10. Contacting the upper face of the rack 10 remote from the teeth thereof is a supporting member 12 which is rigidly attached to the handle 3, so that the rack cannot give way under the influence of the forces exerted thereon and thereby a reliable interengagement of the locking elements 9 and 10 is guaranteed.

The parts 1-12 described so far of the embodiments disclosed herein are, just as their normal operation, known per se. It is observed, that also specula are known, of which the spreading members and the operating members associated therewith are not pivotally but slidably interconnected and in which again associated with each spreading member is one of two co-operating locking elements. Moreover, in a hinged speculum-structure it is possible that the two co-operating locking elements are mounted in places quite different from that shown in the drawing, say in the vicinity of the pivot. Also other variations are possible. Finally it has been suggested to have the free ends of the two handles pointed away from each other.

In the specula of various types known up to now generally one of the two co-operating locking elements is biased, mostly by an elastic initial force, which causes the interengagement of the locking elements. This has the effect that the locking elements are continuously in contact with one another. When, after the duck bill has been inserted into the vagina, the spreading members of such a speculum are brought into the spread positions required for the examination by means of the handles, the co-operating locking elements move one over the other under the influence of the mentioned initial force with a rasping or rattling sound, which often gives the examined woman a very unpleasant sensation and makes the examination more difficult as a result of her reaction.

As will be explained with the aid of two embodiments the invention makes it possible to avoid the disadvantages of the various specula mentioned hereinbefore.

In the speculum shown in FIGS. 1A and 1B the said undesired phenomenon would occur, if the catch 9 and/or the toothed rack 10 should be biased towards one another, owing to which the bevelled end 9 during movement of the handles 3 and 4 towards each other would rasp or rattle over the teeth of the rack 10. However, due to the present invention this phenomenon will not occur.

Namely, it is proposed according to the invention to expose the catch 9 and the toothed rack 10, generally the two co-operating locking elements, to an initial force which pushes these elements away from each other before the spreading members 1 and 2 are brought into spread positions.

Thus the catch 9 of the speculum is entirely free from the teeth of the rack 10 (see distance d), when it is in its disengaged position of rest shown in FIG. 1B. This rack is capable of performing a practically noiseless longitudinal movement between the catch 9 and the supporting member 12, when the members 1 and 2 are spread. After the required open condition has been attained, the examining physician or other examinator has to make the two locking elements 9 and 10 engage with one another by a conscious manipulation. To that end the catch 9 of the described embodiment is provided with a rib 13 to be contacted by the thumb for forcing the catch into engagement with the toothed rack 10.

In the embodiment shown in FIGS. 1A and 1B the catch 9 and its rib 13 are so formed or attached to the handle 3, as to be biased in a direction away from the rack 10 (see the arrow $F_1$ in FIG. 1A). It is then possible but not necessary that the toothed rack 10 is forced with its upper surface against the supporting member 12 by an initial stress. It is observed that also a catch 9 without a rib 13 for the thumb may be used. Then the catch 9 has only a surface area to be contacted by the thumb.

It will be obvious, that the catch 9 in the embodiment illustrated in FIGS. 1A and 1B can be brought into engagement with the rack 10 by a conscious action, that means by manipulation of the rib 13 only and that, before the desired spread positions of the spreading members 1 and 2 are attained, the catch does not touch said rack. As soon as the catch has been brought, after the speculum has been spread, into engagement with the rack by manipulation of the rib to be contacted by the thumb it is held in place by the forces exerted in the closing direction on the spreading members 1, 2 by, for instance, the tissue surrounding an expanded body cavity which forces are transmitted through said members and the handles 3 and 4 on the catch 9 and the rack 10. When, after the examination has been finished, the two handles 3 and 4 are moved towards each other through a small distance only, the bevelled upper end of the catch 9 is able to escape from the toothed rack, so that the catch then returns by its initial stress in the direction of the arrow $F_1$ to its position shown in FIG. 1B, in which position it is out of the reach of the rack 10 and the locking does not exist anymore. Thereafter the spreading members 1 and 2 can be brought into their closed positions and removed from the body cavity. During this action no undesired noise occurs.

In the embodiment shown in FIG. 2 and described hereinafter only the details which are important as far as the invention is concerned are illustrated in said figure. Only portions of the handles are shown.

FIG. 2 shows on a larger scale a sectional view of a detail of another embodiment of the speculum according to the invention. Therein a toothed rack 20 is used which is also curved but cooperates, in its locking positions, with the upper edge 19 of a window 21 made in the handle 3, through which it extends. The supporting strip 25 is divergent or spaced away from the surface of handle 4 at a point below the notch 27 to allow rack 20 and its free end 23 to be normally biased away from the upper edge 19 of window 21. The rack 20 can be forced into a locking position by a conscious action of the person using the speculum. This person must bring the rack into engagement with the upper edge 19 of the window by touching with his thumb or his hand the free end 23 of the rack, which free end may be compared with the rib 13 shown in FIG. 1. The locking operation may also be carried out by forcing the supporting strip 25 against the handle 4. If this does not happen, the toothed rack will stay pressed with is lower side against the lower edge 22 of the window 21 by its initial stress. The rack, which in this embodiment is able to move freely through a window 24 provided in the other handle 4, is held biased by a supporting strip 25 which is formed on the rack and is fixed to the outside of the handle 4 by fastening means 26 made of synthetic material or metal. The initial stress set up in the supporting strip 25 in the region near a notch 27 during its manufacture is transmitted on the rack 20 through the lower end of the supporting strip 25.

It will be apparent, that in the embodiment shown in FIG. 2 the toothed rack 20 only engages with the upper edge 19 of the window 21 of the handle 3, if it is forced against said edge by a consciously exerted pressure on its free end 23 or on the supporting strip 25. As long as this does not happen, the rack stays clear of the upper edge, so that during the spreading of the associated duck bill no undesired noise can occur.

As appears from what is said hereinbefore the invention provides various embodiments of a speculum comprising locking elements which are associated with the spreading members and, during the spreading movement of said members, are free from forces acting in the direction of their mutual engagement, so that during the just mentioned manipulation there are no interfering noises.

The invention is not restricted to the embodiments described hereinbefore and illustrated in the drawing. Several modifications may be applied in the described details and in the mutual conjuction thereof, without transgression of the scope of the invention.

What is claimed is:

1. A speculum comprising:

cooperating first and second spreading members movable relative to one another between a closed position, to allow for insertion thereof into a body cavity, and a discrete, adjustable open position, to allow for medical inspection of said body cavity, said spreading members each including a handle element coupled thereto for moving said spreading members between said open and closed positions thereof; and means for releasably locking said spreading members in optionally determinable, discrete open positions, said locking means including a first locking element and a second locking element configured for mutual, releasable engagement with one another, each of which is coupled respectively to said first and second spreading members for movement therewith, with at least one of said locking elements being normally biased in a direction away from engagement with the other locking element, so as to require positive manual force to move said locking elements into mutual engagement and thereby releasably lock said spreading members in a desired open position, and so as to prevent undesired noises during movement of said spreading members between said open and closed positions by substantially eliminating contact between said locking elements during such movement.

2. The speculum according to claim 1, additionally including finger abutment means on one of said locking elements to assist in manual movement thereof into mutual engagement with said other locking element.

3. The speculum according to claim 2, wherein one of said locking elements is a toothed member and the other locking element is shaped to releasably lockingly engage with the toothed member and wherein said finger abutment means comprises a thumb grip-configured surface provided on said other locking element.

4. The speculum according to claim 1, wherein said spreading members are pivotably coupled together.

5. The speculum according to claim 1, wherein one of said locking elements is a toothed member and wherein said other locking element comprises an upper edge of a window made in the handle element of the spreading member to which it is coupled and through which window said toothed member extends and wherein said toothed member is normally biased in a direction away from said upper edge of said window.

* * * * *